(12) United States Patent
Bae Park (10) Patent No.: US 7,441,737 B2
(45) Date of Patent: Oct. 28, 2008

(54) SUNGLASSES HOLDER

(76) Inventor: Seung Bae Park, 1310-1106 Cholsanjugong Apt., Choisan 3-Dong, Gwangmyung City, Gyanggi-Do 423-737 (KR)

(*) Notice: Subject to any disclaimer, the term of this patent is extended or adjusted under 35 U.S.C. 154(b) by 238 days.

(21) Appl. No.: 10/519,389

(22) PCT Filed: Jul. 1, 2003

(86) PCT No.: PCT/KR03/01290

§ 371 (c)(1), (2), (4) Date: Dec. 23, 2004

(87) PCT Pub. No.: WO2004/006001

PCT Pub. Date: Jan. 15, 2004

(65) Prior Publication Data

US 2005/0263661 A1 Dec. 1, 2005

(30) Foreign Application Priority Data

Jul. 2, 2002 (KR) .................. 20-2002-0019837 U (51) Int. Cl.
*E04G 3/00* (2006.01)
(52) U.S. Cl. ............... 248/292.12; 16/381; 16/334; 403/96; 403/97; 403/326; 2/10; 248/291.1
(58) Field of Classification Search ........... 248/291.1, 248/220.21; 16/342, 271, 257, 258, 330, 16/334, 381; 24/614, 615; 403/326, 329, 403/14, 13, 96, 97, 101; 2/9, 10, 13
See application file for complete search history.

(56) References Cited

U.S. PATENT DOCUMENTS

| 2,435,225 | A | * | 2/1948 | Kolodner et al. ............ 30/519 |
| 2,459,386 | A | * | 1/1949 | Matthes ........................ 403/97 |
| 4,407,044 | A | * | 10/1983 | Iseki ............................ 16/237 |
| 5,361,455 | A | * | 11/1994 | Kiefer .......................... 16/235 |
| 5,412,812 | A | * | 5/1995 | Gatchalian ...................... 2/10 |
| 5,471,259 | A | * | 11/1995 | Cahill ........................ 351/155 |
| 5,581,838 | A | * | 12/1996 | Rocco ......................... 15/110 |
| 5,689,827 | A | * | 11/1997 | Ryder ............................. 2/10 |
| 5,720,040 | A | * | 2/1998 | Simone ........................... 2/10 |
| 5,920,371 | A | * | 7/1999 | Chang et al. ................ 351/158 |
| 5,933,919 | A | * | 8/1999 | Miller et al. ................. 16/244 |
| 5,987,640 | A | * | 11/1999 | Ryder ............................. 2/10 |
| 6,481,060 | B1 | * | 11/2002 | Tsai ........................... 24/3.12 |

(Continued)

FOREIGN PATENT DOCUMENTS

JP 5892331 6/1983

(Continued)

*Primary Examiner*—Kimberly T. Wood
(74) *Attorney, Agent, or Firm*—Bell, Boyd & Lloyd LLP (57) ABSTRACT

Sunglass holder with built-in clip for attachment and detachment can be used on industrial sites besides sports type of hat (cap) by being conjoined with the sunglass and goggle of military helmet. When fishing at the desert where wind of sand is rampant, river or ocean, it protects the eyes from the sand and ultraviolet rays from sunlight. Towards this end, it is possible to use by conjoining hat and sunglass lens, and the product is invented to apply in diverse areas such as sunvisor, cowboy hat beret, knit wool hat, hat and hair band for jogging etc.

10 Claims, 10 Drawing Sheets

U.S. PATENT DOCUMENTS

| | | |
|---|---|---|
| 6,599,050 B1 * | 7/2003 | Sjoo ............................ 403/97 |
| 6,611,991 B2 * | 9/2003 | Okeke et al. .................. 16/225 |
| 6,848,344 B2 * | 2/2005 | Rocco ....................... 81/177.8 |
| 2001/0023518 A1 * | 9/2001 | Okeke et al. .................. 16/225 |

FOREIGN PATENT DOCUMENTS

| | | | |
|---|---|---|---|
| JP | 669232 | | 9/1994 |
| JP | 2000083709 | * | 3/2000 |
| KR | 1020020066148 | | 8/2002 |
| WO | WO9530923 | | 11/1995 |

* cited by examiner

SUNGLASSES HOLDER

TECHNICAL FIELD

The present invention relates to a sunglasses holder. More particularly, the invention relates to a sunglasses holder capable of combining a pair of sunglasses with a cap, a woolen cap, a jogging hair-band, a sports cap (suncap), a sun visor, a helmet, and the like.

BACKGROUND ART

In general, a sunglasses is composed of a pair of lenses, a pair of rims and a pair of legs, and has been used for shielding sunlight. Recently, it also is used as a fashionable accessory, along with the above inherent purpose.

However, when the user wears the sunglasses described above, the around of his or her nose and ears become moist with perspiration due to a nose support, i.e., a bridge of the rim and the legs. In addition, he or she may feel uncomfortably due to the weight of the sunglasses. In particular, when the user wears a cap together with a sunglasses, it makes the user more uncomfortable.

In order to overcome these problems in the prior art, a sunglasses affixed to a cap has been proposed, but it has a problem in that a user cannot select a cap, depending on his or her preference.

DISCLOSURE OF INVENTION

The present invention has been made to solve the above problems occurring in the prior art, and it is an object of the invention to provide a sunglasses holder, which is suitable for combining a pair of sunglasses with a cap, a woolen cap, a jogging hair-band, a sports cap (suncap), a sun visor, a helmet, and the like, depending on a user's preference.

Another object of the invention is to provide a sunglasses holder being capable of detachably attaching a pair of sunglasses to a cap and the like.

A further object of the invention is to provide a sunglasses holder, in which the angle adjustment thereof is easily carried out.

In order to accomplish the above objects, according to one aspect of the present invention, there is provided a sunglasses holder, which is suitable for combining a pair of sunglasses with a cap, a woolen cap, a jogging hair-band, a sports cap (suncap), a sun visor, a helmet, and the like. The sunglasses holder of the invention comprises: a fixing member having a fixing means for fixing to the cap or the like; a connection member being connected to the sunglasses; and hinges formed respectively in the fixing member and the connection member, the hinges being rotatably coupled to each other by a hinge pin and having a toothed wheel formed in the side wall such that they are engaged with each other, thereby enabling an adjustment of angle.

According to another aspect of the invention, there is provided a sunglasses holder, which is suitable for combining a pair of sunglasses with a cap, a woolen cap, a jogging hair-band, a sports cap (suncap), a sun visor, a helmet, and the like, and can be carried in a disassembled state when not in use. The sunglasses holder of the invention comprises: a fixing member including a body having an opening formed at the under face and a hole formed at both sides thereof, a resilient piece having a button projected through the hole, and a fixing means for fixing the body to the cap or the like; a detachably-attaching member inserted into the opening of the fixing member to be coupled with the fixing member, the detachably-attaching member having a resilient hook formed such that it can be released from the fixing member by pressurizing the resilient piece; a connection member coupled to the sunglasses; and hinges formed respectively in the fixing member and the connection member, the hinges being rotatably coupled to each other by a hinge pin and having a toothed wheel formed in the side wall such that they are engaged with each other, thereby enabling an adjustment of angle.

Preferably, the fixing means of the fixing member may include a bolt, a support plate is integrally formed at both sides of the body, and the support plate has a hole for the bolt to pass through, thereby enabling a bolt coupling.

Preferably, the respective hinge or either of them has a female thread form at the inner circumference thereof, and the hinge pin has a male thread formed at the outer circumference thereof, correspondingly to the female thread.

BRIEF DESCRIPTION OF DRAWINGS

Further objects and advantages of the invention can be more fully understood from the following detailed description taken in conjunction with the accompanying drawings, in which.

BEST MODE FOR CARRYING OUT THE INVENTION

The construction and operation of the embodiments of the invention will be explained in detail with reference to the accompanying drawings.

Figure 1A:
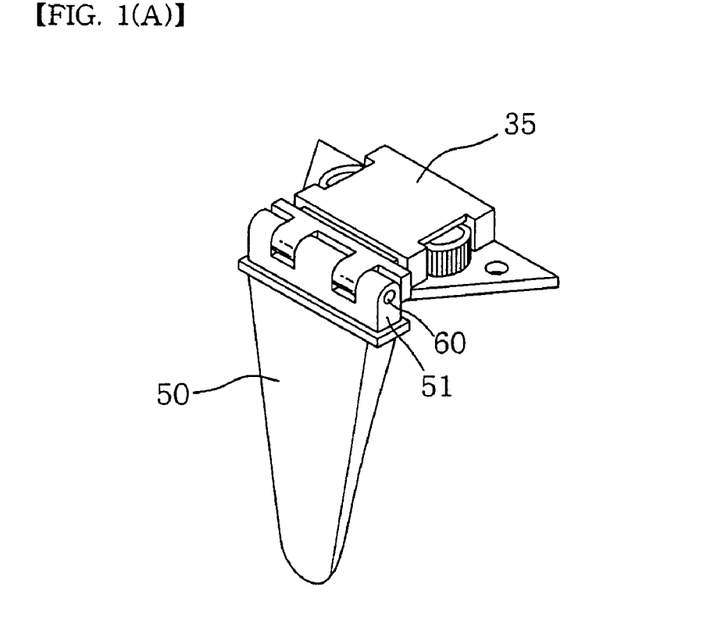
FIG. 1(A) is a perspective view showing a sunglasses holder according to a first embodiment of the invention.

FIG. 1(A) is a perspective view of a free detachable sunglasses holder according to a first embodiment of the invention.

Referring to FIG. 1(B) to 4(C), the first embodiment of the invention comprises a fixing member 30, a detachably-attaching member 40, and a connection member 50.

Figure 1B:
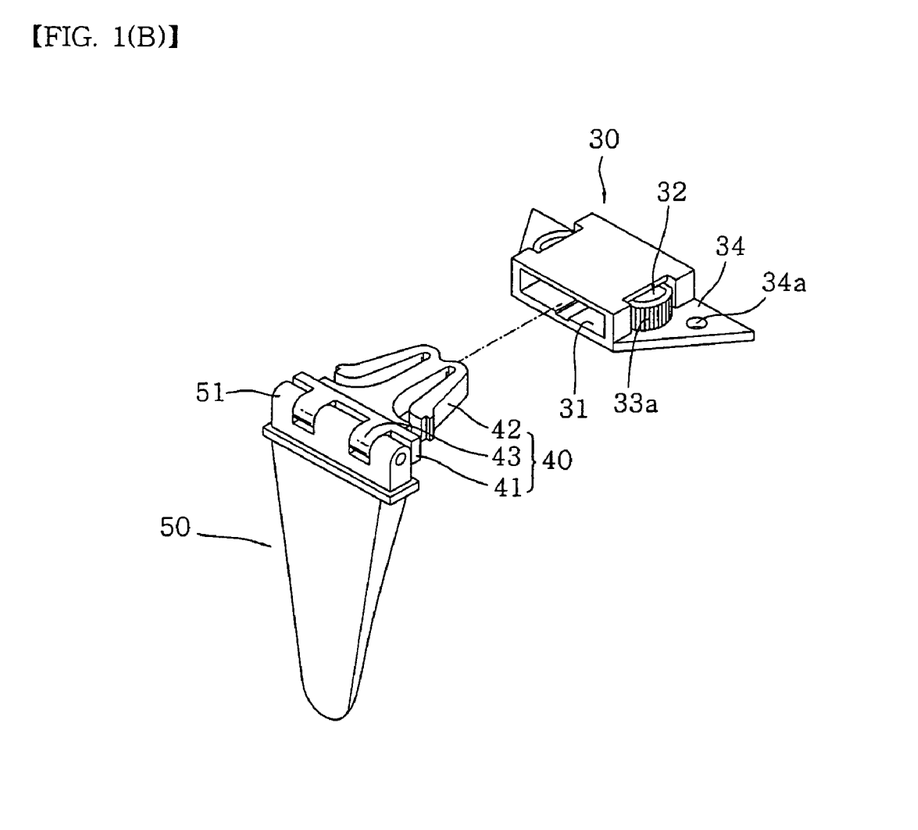
FIG. 1(B) is a perspective view of the sunglasses holder of FIG. (A), where a fixing member and a detachably-attaching member are separated.

The fixing member 30 includes a body 35 having an opening 31 provided at the lower portion thereof and a hole 32 provided at both sides thereof. The body 35 is provided, at the side portion thereof, with a support plate 34 integrally formed therewith, and the support plate 34 has a through-hole 34a formed therein, through which a bolt is to pass. The sunglasses holder of the invention is fixed to the bottom portion or front face a cap visor, or to a sports cap by means of a bolt passing through the through-hole 34a. A resilient piece 33 is housed inside the fixing member 30, and the resilient piece 33 has a pressurizer 33a projected through the hole 32.

The detachably-attaching member 40 includes a base 41, a resilient hook 42, and a hinge 43 formed integrally together. The resilient hook 42 is constructed such that it is inserted into the opening 31 of the fixing member, and its both ends are fixed by one side wall of the hole 32. It is also configured such that the resilient hook 42 constrained by the hole 32 can be released from the fixing member 30 by pressurizing the resilient piece 33.

The connection member 50 has a connection pin 52 formed at one end thereof, by which a pair of sunglasses can be assembled thereto.

Figure 2:
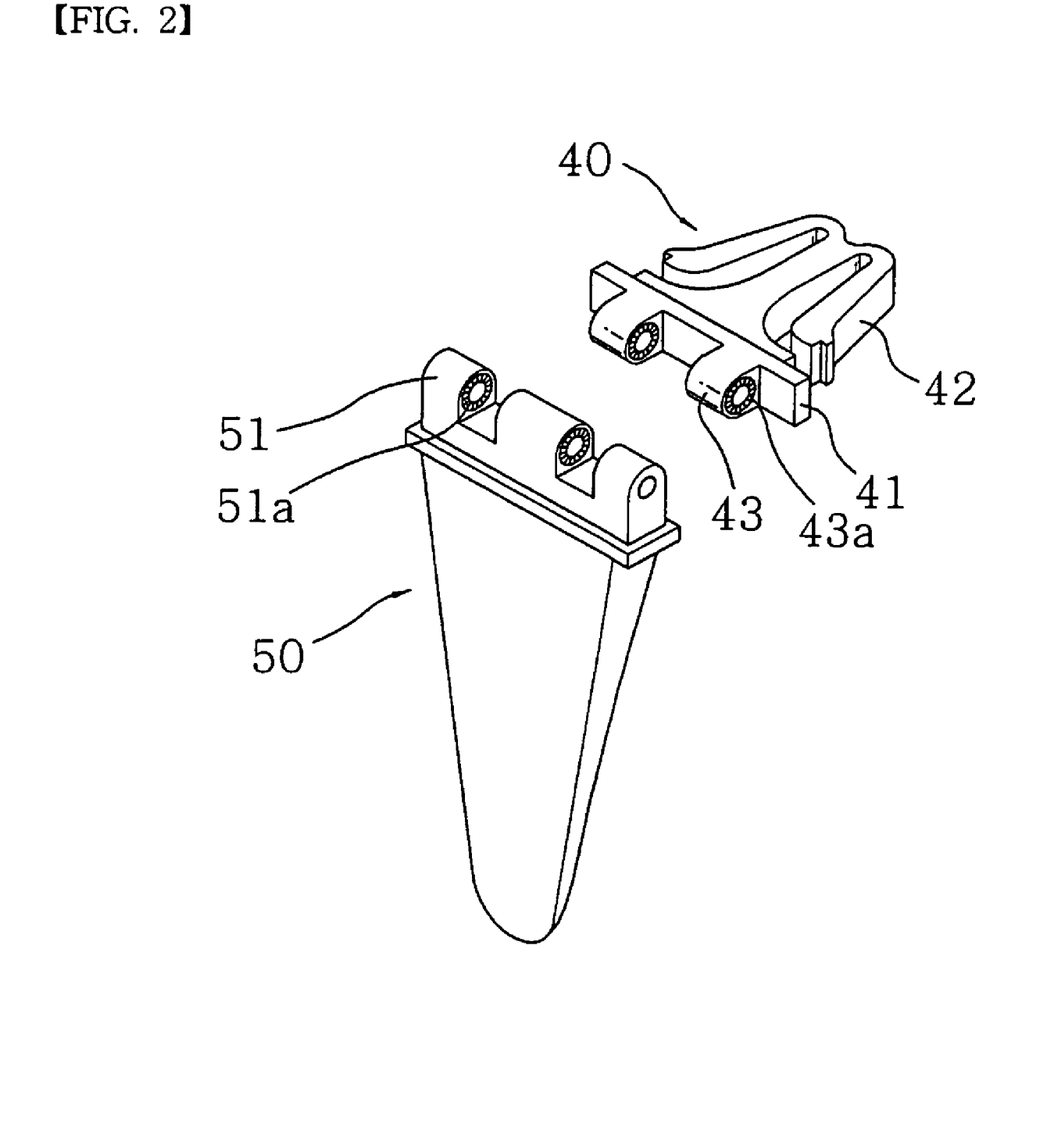
FIG. 2 is a perspective view of the sunglasses holder of FIG. (A), where a detachably-attaching member and a connection member are separated.
Figure 3A:
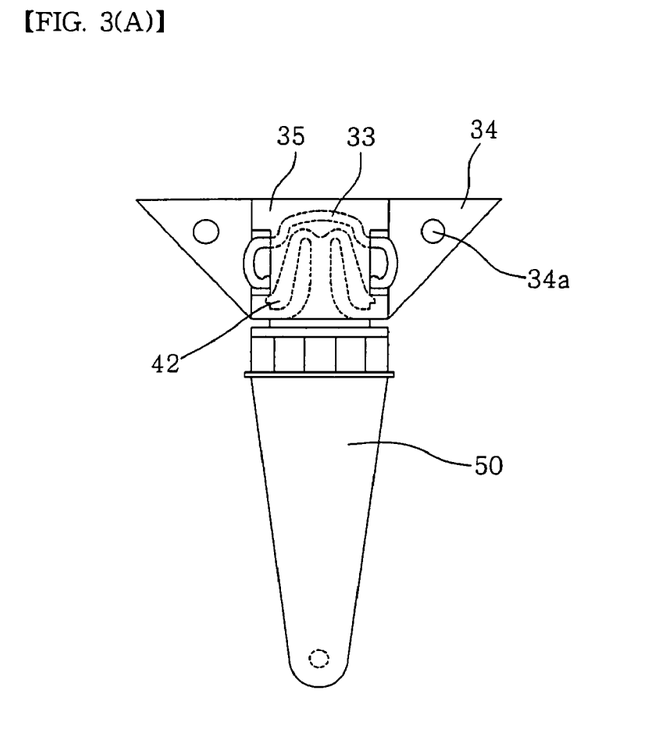
FIGS. 3(A) and 3(B) are a rear view and a side view showing the assembled state of the first embodiment of the invention.
Figure 3B:
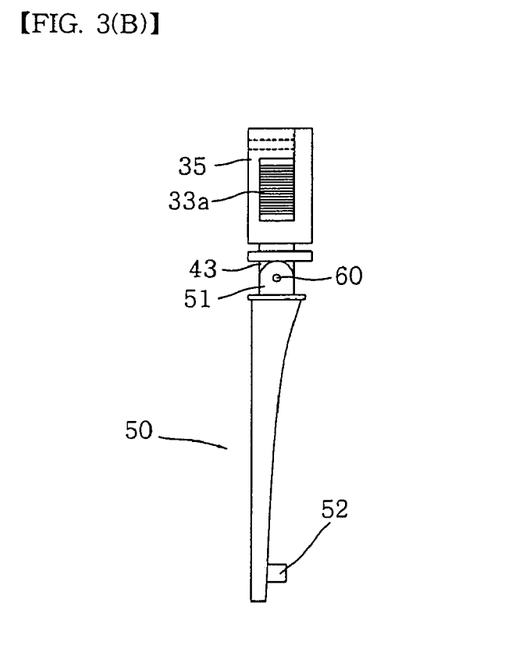

The hinges 43, 51 are constructed in such a manner that the lower portion of the base 41 and the upper portion of the connection member 501 are rotatably coupled to each other by a hinge pin 60. In particular, as shown in FIG. 2, the both hinges 43, 51 have toothed wheels 43a, 51a engaged with each other at their side walls, so that the detachably-attaching member 40 and the connection member 50 can be pivotally rotated with respect to each other and can be remained strictly at a desired adjusted angle.

Figure 4A:
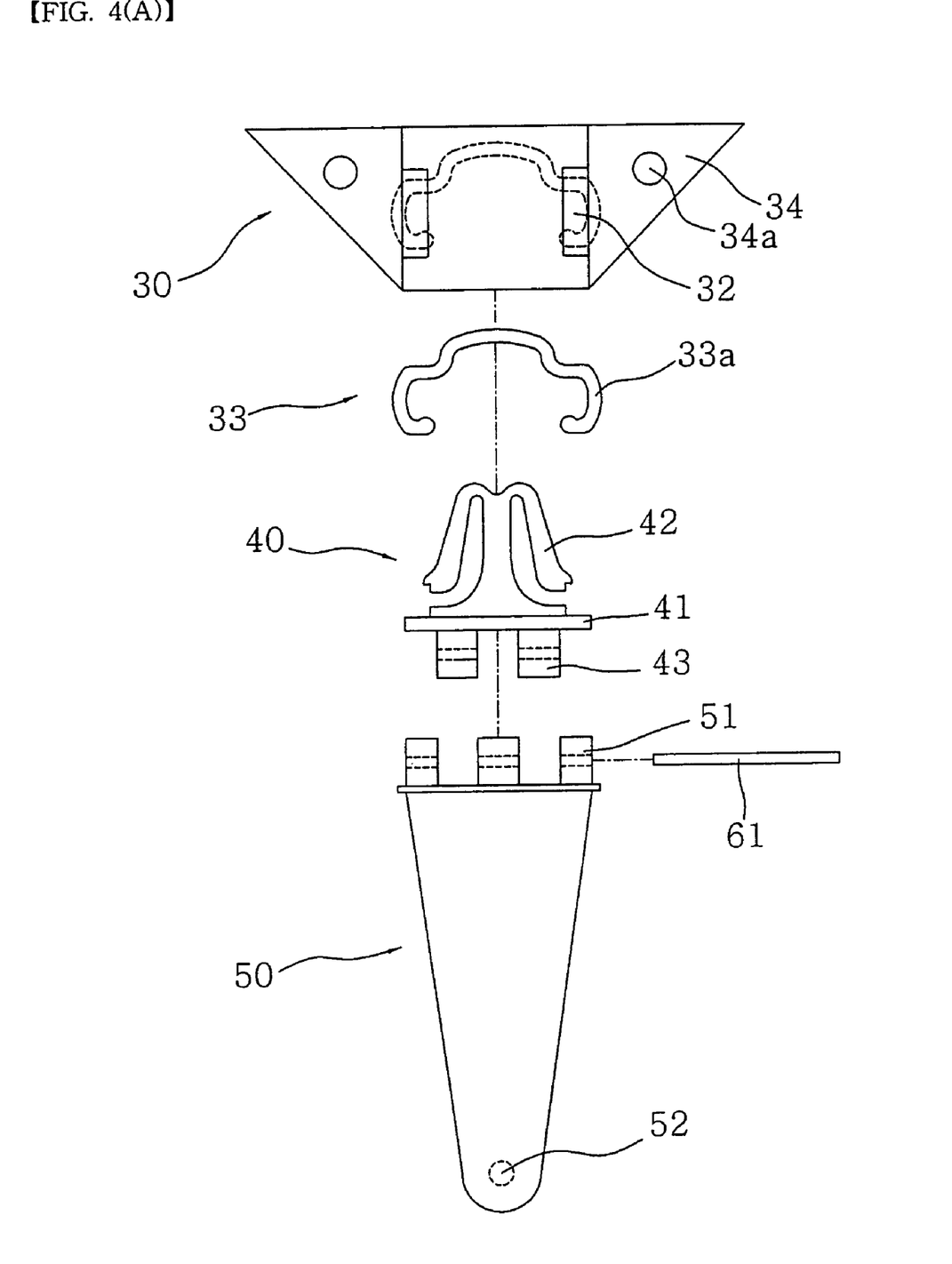
FIGS. 4(A) and 4(B) are a rear view and a side view showing the disassembled state of the first embodiment of the invention.
Figure 4B:
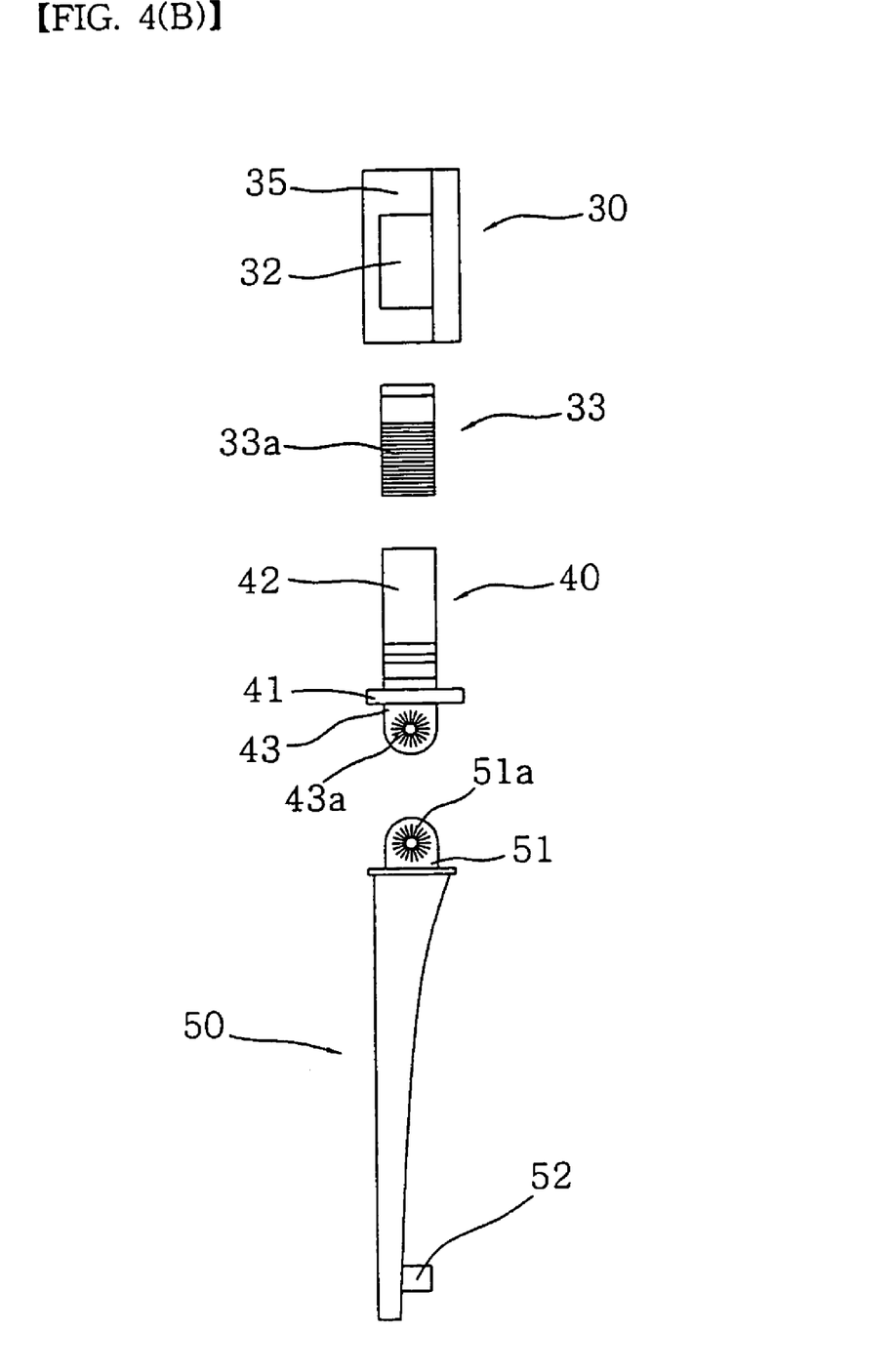
Figure 4C:
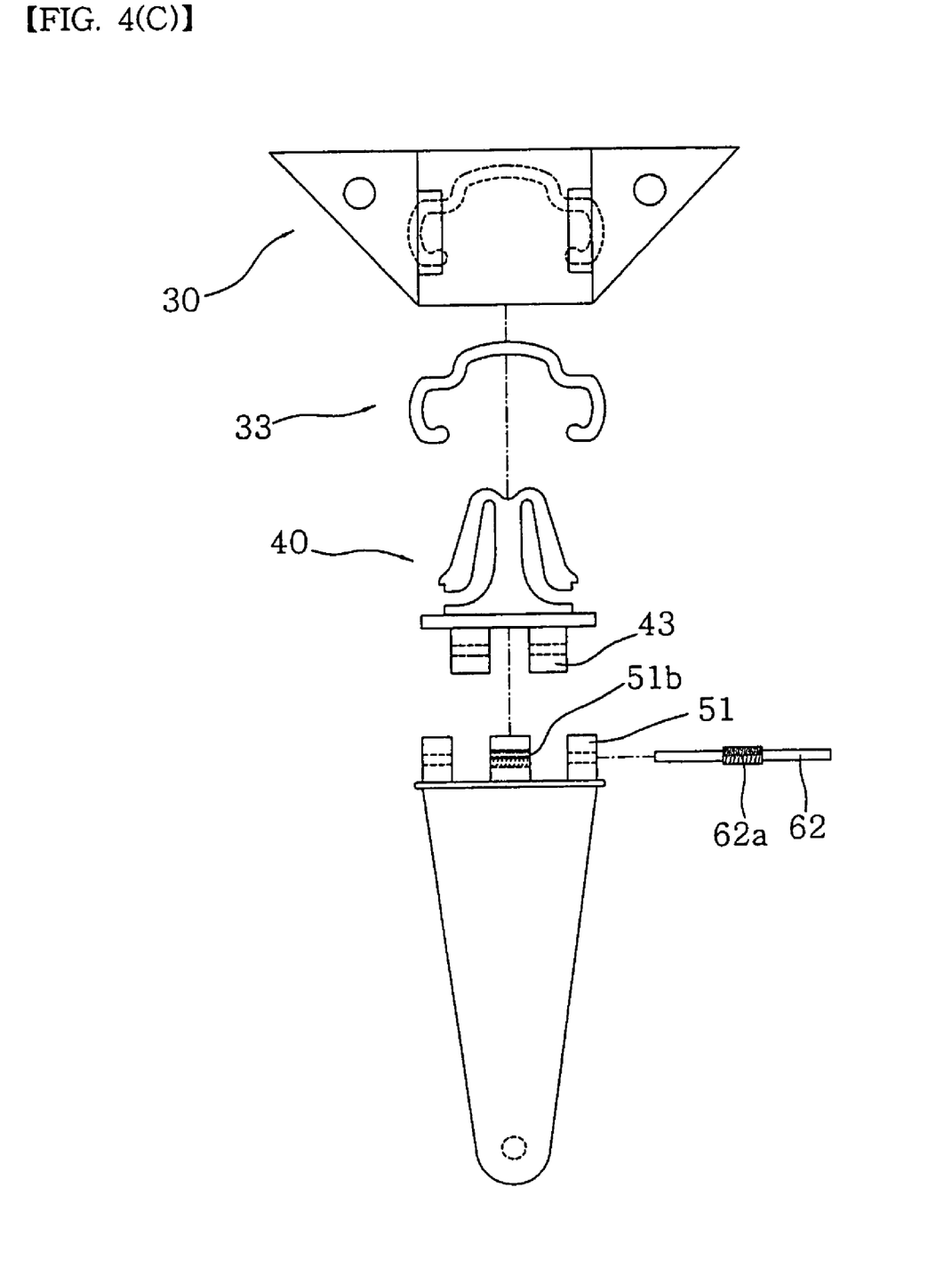
FIG. 4(C) is a rear view showing another embodiment having a hinge different from that of FIG. 4(A)

Referring to FIGS. 4(A) and 4(C), it will be seen that the hinges 43, 51 and the hinge pin 61, 62 have a different construction from each other. That is, as shown in FIG. 4(A), a typical hinge pin 61 can be employed for connection, but the hinges 43, 51 and the hinge pin 61 are structured to be thread-engaged with each other. More specifically, the hinge 51 formed above the connection member 50 has a female thread formed in the inner circumference thereof, and correspondingly the hinge pin 62 has a male thread formed in the outer circumference thereof. Therefore, the hinges 43, 51 are fitted together and the hinge pin 62 is thread-inserted thereinto to thereby connect them. This construction prevents the hinge pin 62 from being escaped from the sunglasses holder, which may happen in a long-term use of it. Also, it enables sunglasses angle to be adjusted and the adjusted angle to be remained correctly as adjusted.

Figure 5:
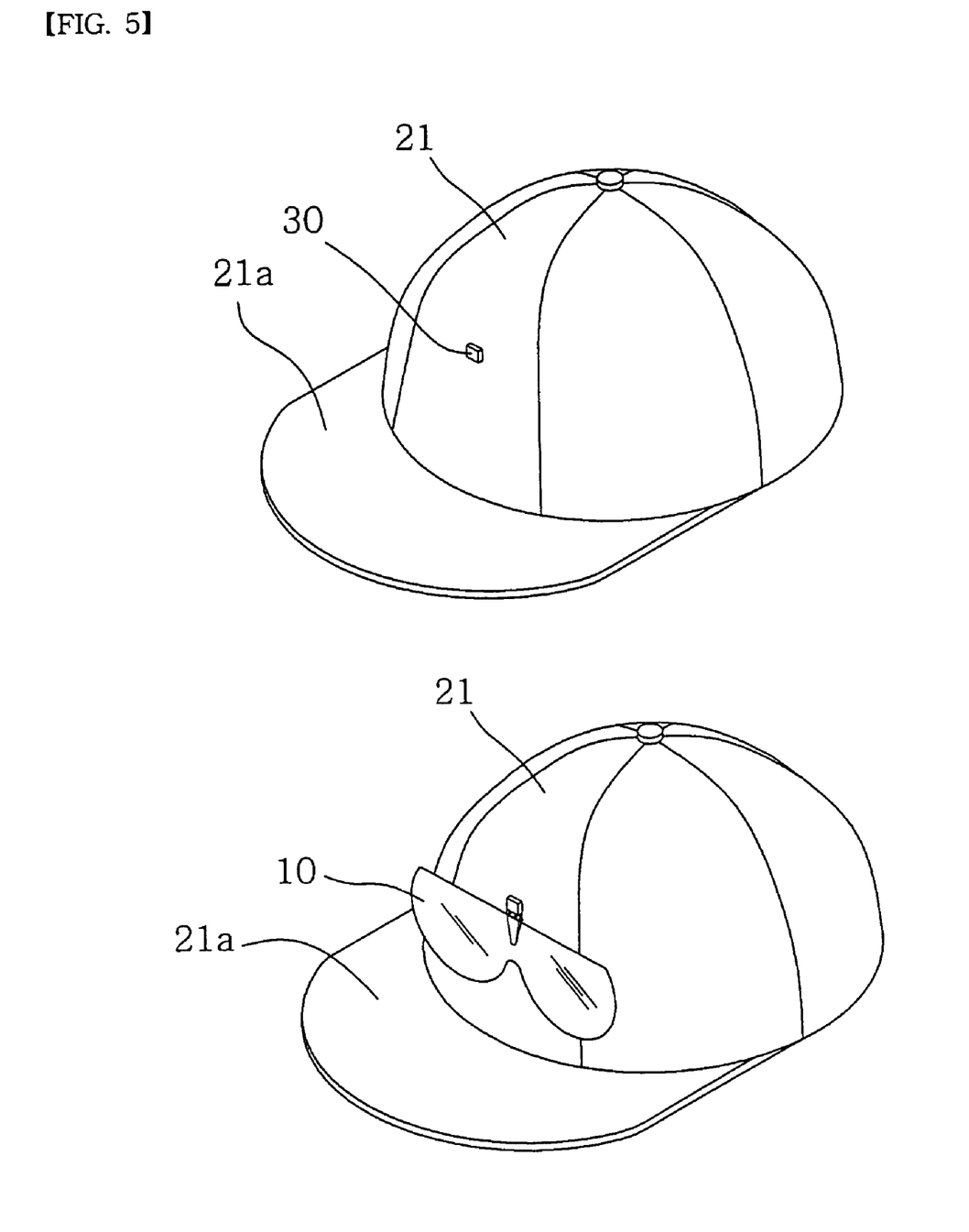
FIG. 5 shows caps having respectively a fixing member attached above the visor thereof and a sunglasses holder of the invention assembled to the fixing member.
Figure 6A:
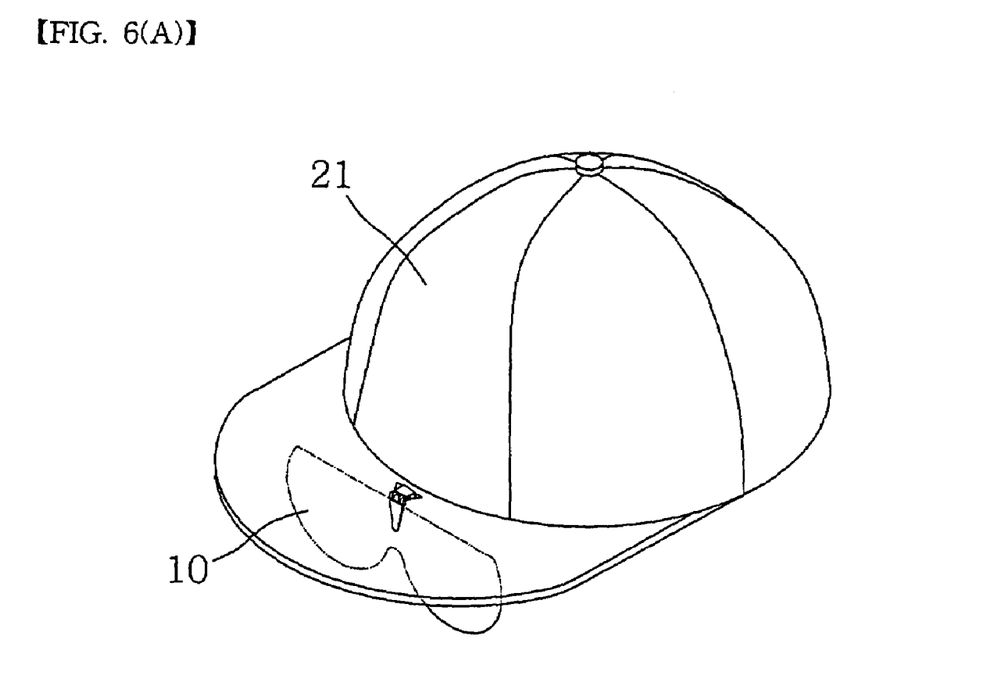
FIG. 6(A) shows a sunglasses assembled to the sunglasses holder of the invention.
Figure 6B:
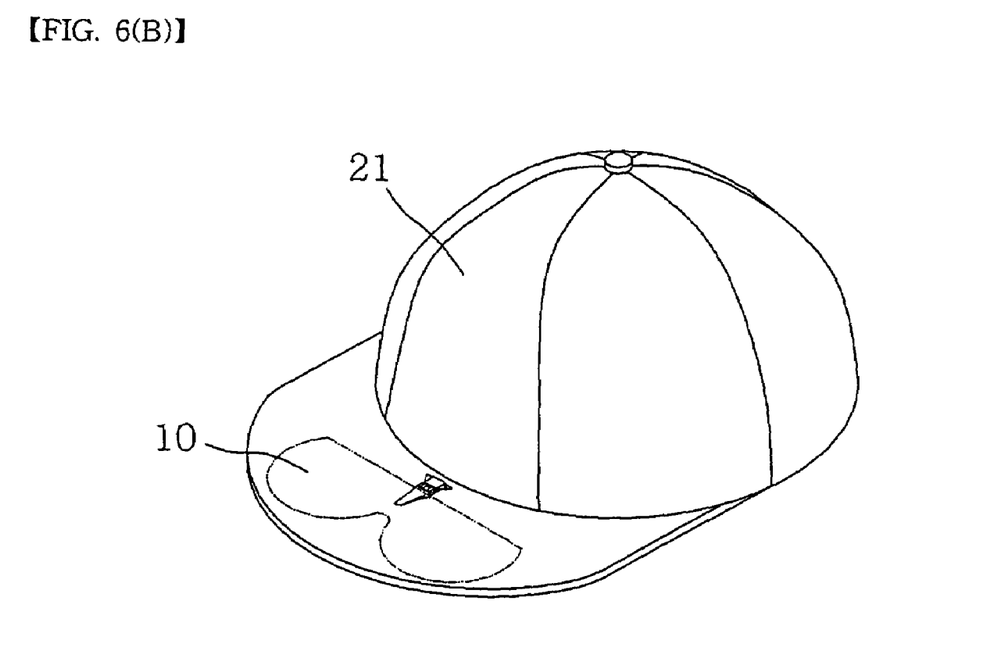
FIG. 6(B) shows the sunglasses turned to the upper position.

FIG. 5 shows caps having respectively the fixing member 30 attached above the visor 21a thereof (the front face of the cap) and a pair of sunglasses 10 assembled above the visor 21a. Among young people and sports men, recently, the sunglasses has been used as a fashionable accessory, along with the purpose of shielding the sunlight. The example in FIG. 5 is to conform to this recent tendency. Furthermore, if the fixing member 30 of the invention is fixed both above and below the cap visor 21a, the sunglasses 10 can be selectively attached to either of them, depending on the circumstances Referring to FIGS. 6(A) and 6(B), the sunglasses 10 can be used for shielding sunlight as shown in FIG. 6(A), and when desired, can be turned upwards as shown in FIG. 6(B). Therefore, when the sunglasses 10 is not needed temporarily, it can be turned upwards by simply operating to pressurize the resilient piece 33, without removing the detachably-attaching member 40. According to the invention, it is understood that both hinges 43, 51 have the toothed wheels 43a, 51a formed in the side wall thereof and engaged with each other, and therefore, once the sunglasses 10 is turned upwards, it will not fall down voluntarily unless the user pushes it down.

Figure 7A:
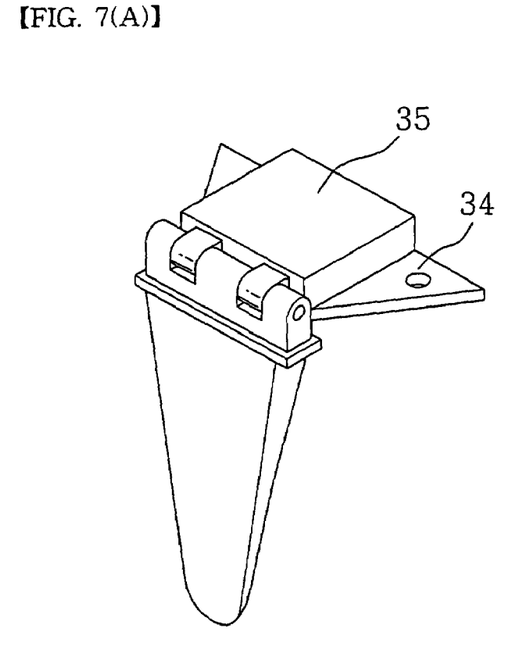
FIGS. 7(A) and 7(B) illustrate a sunglasses holder according to a second embodiment of the invention.
Figure 7B:
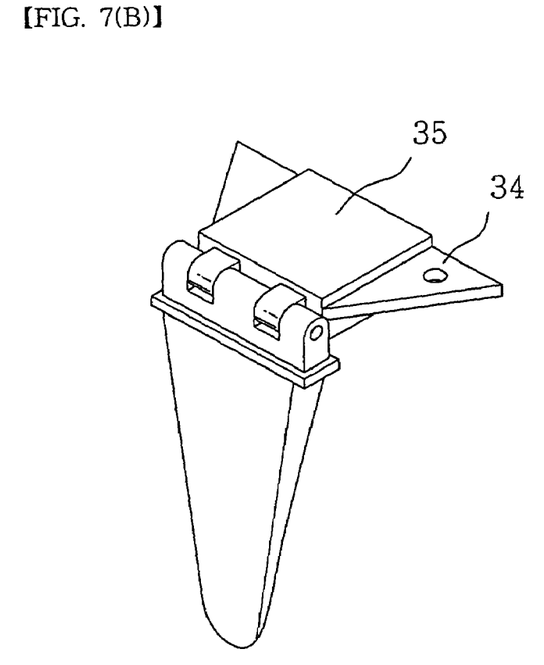

FIGS. 7(A) and 7(B) illustrate a second embodiment of the invention. The second embodiment is different from the first one in that there is no detachably-attaching member 40. That is, the second embodiment is composed of a fixing member 30 and a connection member 50. The fixing member has a support plate 34 formed at both sides thereof, and the support plate 34 is provided with a through-hole 34a, through which a bolt is to pass. The connection member 50 is rotatably coupled to the fixing member at one side and, at the other side, can be connected to the sunglasses 10. It also is preferable in the second embodiment that the both hinges have toothed wheels 43a, 51a engaged with each other at the side wall thereof. According to the second embodiment, therefore, a sunglasses holder having no detachable function is provided. In addition, as shown in FIGS. 7(A) and 7(B), the fixing member 30 and the connection member 50 may be switched to each other, in which the construction of FIG. 7(A) is suitable for the upper face of a cap visor 21a or a hair band 24 and that of FIG. 7(B) is suitable for the lower portion of the cap visor 21a.

Figure 8A:
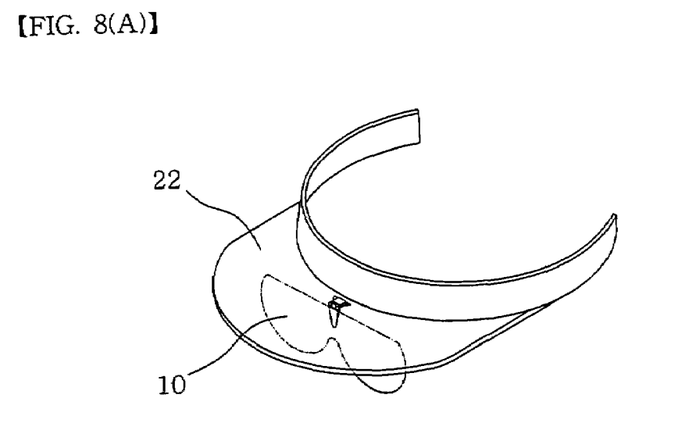
FIGS. 8(A) to 8(C) show the sunglasses holder attached to a sun visor, a woolen cap, and a jogging hair-band.
Figure 8B:
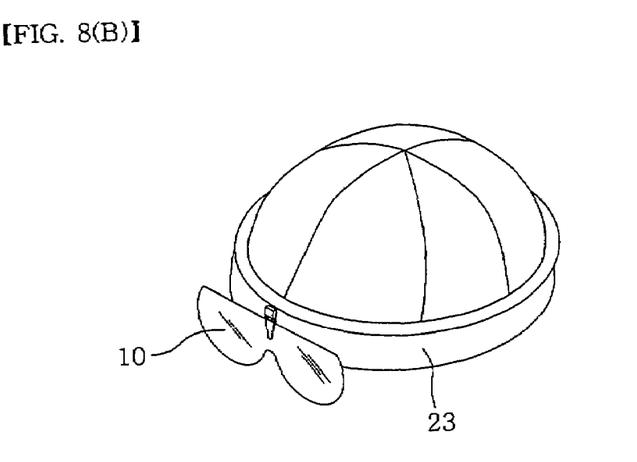
Figure 8C:
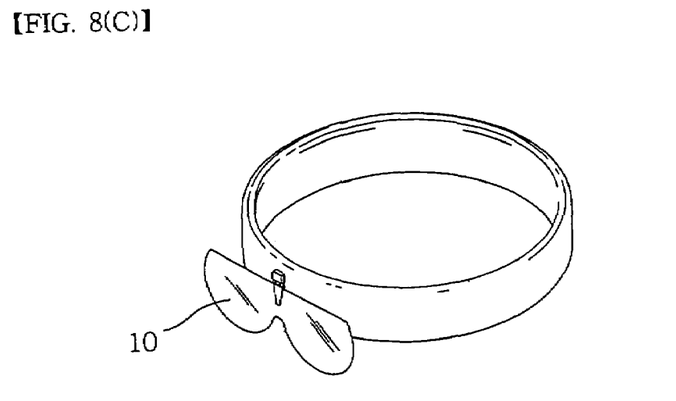

FIGS. 8(A) to 8(C) show the sunglasses holder attached under the visor of a sun visor 22, a woolen cap 23, and a jogging hair-band 24 when in use. In particular, the fixing member 30 shown in FIGS. 8(B) and 8(C) has no support plate. The support plate has a through-hole formed at the side thereof for a bolt to pass through. Therefore, in the case where the fixing member 30 is exposed to the outside, the outer appearance is not spoiled, such as when the sunglasses holder is used for the upper portion of a cap visor 21a, a woolen cap 23 and a jogging hair-band 24.

INDUSTRIAL APPLICABILITY

According to the sunglasses of the invention, various caps and sunglasses lenses can be selected and combined therewith, depending on user's preference, and the user can carry it in a disassembled state.

In addition, the user can have a pleasant feeling when worn since it does not need a rim and legs.

Also, the angle of sunglasses can be freely adjusted due to its hinges, and the adjusted angle can be accurately maintained by means of the engagement of the toothed wheels formed in the side walls thereof.

Furthermore, an additional fixing member can be fixed above a cap visor, and thus, when needed, the sunglasses holder can be applied to the upper and lower portion of the cap visor, thereby providing various uses.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A sunglasses holder, which is suitable for coupling a pair of sunglasses to an item worn on a head of a wearer comprising:
   a) a fixing member for attachment to the item;
   b) a connection member for attachment to the sunglasses; and
   c) hinges formed respectively in the fixing member and the connection member, each of the hinges having an axis of rotation and including at least one sidewall perpendicular to the axis of rotation, the sidewalls each having a toothed wheel formed therein, the hinges being rotatably coupled to each other by a hinge pin insertable through said hinges, and the toothed wheel of the fixing member hinge engaged with the toothed wheel of the connection member hinge, thereby enabling an adjustment of angle between the fixing member and the connection member, wherein the hinge pin includes a male threaded portion corresponding to a female threaded portion of the connection hinge, and the hinge pin includes non-threaded portions that correspond to the fixing member hinge.

2. A sunglasses holder, which is suitable for coupling a pair of sunglasses to an item worn on a head of a wearer and can be carried in a disassembled state when not in use, comprising:

a) a fixing member including a body defining an interior space, the body including at least a first wall and a second wall each having a hole formed therein, a resilient piece coupled to each of the first wall and the second wall and having a button projected through the respective holes, and a fixing means for attachment of the body of the fixing member to the item;

b) a detachably-attaching member inserted into the interior space of the fixing member to be coupled with the fixing member, the detachably-attaching member having a resilient hook formed such that it can be released from the fixing member by pressurizing the resilient piece;

c) a connection member for attaching to the sunglasses; and d) hinges formed respectively in the detachably-attaching member and the connection member, each of the hinges having an axis of rotation and including at least one sidewall perpendicular to the axis of rotation, the sidewalls each having a toothed wheel formed therein, the hinges being rotatably coupled to each other by a hinge pin insertable through the hinges, and the toothed wheel of the fixing member hinge engaged with the toothed wheel of the connection member hinge, thereby enabling an adjustment of angle between the detachably-attaching member and the connection member, wherein the hinge pin includes a male threaded portion corresponding to a female threaded portion of the detachably-attaching member hinge, and the hinge pin includes non-threaded portions that correspond to the fixing member hinge.

3. A sunglasses holder according to claim 1, wherein the fixing member includes a bolt, a support plate is integrally formed at both sides of the body, and the support plate has a hole for the bolt to pass through, thereby enabling a bolt coupling.

4. A sunglasses holder according to claim 1, wherein the fixing member is configured for attachment to an upper portion of the item.

5. A sunglasses holder of claim 1, wherein the item is selected from the group consisting of a cap, a woolen cap, a jogging hair-band, a sports cap, a suncap, a sun visor, and a helmet.

6. A sunglasses holder of claim 2, wherein the item is selected from the group consisting of a cap, a woolen cap, a jogging hair-band, a sports cap, a suncap, a sun visor, and a helmet.

7. A sunglasses holder according to claim 2, wherein the fixing member includes a bolt, a support plate is integrally formed at both sides of the body, and the support plate has a hole for the bolt to pass through, thereby enabling a bolt coupling.

8. A sunglasses holder according to claim 2, wherein the fixing member is configured for attachment to an upper portion of the item.

9. A sunglass holder of claim 4, wherein the item is a cap visor.

10. A sunglass holder of claim 8, wherein the item is a cap visor.

* * * * *